US006372720B1

(12) United States Patent
Longmuir et al.

(10) Patent No.: US 6,372,720 B1
(45) Date of Patent: Apr. 16, 2002

(54) LIPOSOME FUSION AND DELIVERY VEHICLE

(76) Inventors: Kenneth J. Longmuir, 8 Gibbs Ct., Irvine, CA (US) 92612; Alan J. Waring, 12 Melodylane, Irvine, CA (US) 92614; Sherry M. Haynes, 16 Seton Rd., Irvine, CA (US) 92612

( * ) Notice: Subject to any disclaimer, the term of this patent is extended or adjusted under 35 U.S.C. 154(b) by 0 days.

(21) Appl. No.: 09/019,346

(22) Filed: Feb. 5, 1998

(51) Int. Cl.$^7$ ................. A61K 48/00; A61K 9/127
(52) U.S. Cl. ............. 514/44; 424/450; 435/320.1; 435/455; 435/458; 514/2
(58) Field of Search .................. 435/455, 458, 435/320.1; 514/44; 530/350, 323, 326; 424/450

(56) References Cited

U.S. PATENT DOCUMENTS

| | | | |
|---|---|---|---|
| 4,873,089 A | | 10/1989 | Scotto et al. ........... 424/450 |
| 5,006,343 A | * | 4/1991 | Benson et al. .......... 424/450 |
| 5,149,782 A | | 9/1992 | Chang et al. ........... 530/326 |
| 5,169,933 A | * | 12/1992 | Anderson et al. ....... 530/391.3 |
| 5,599,712 A | | 2/1997 | Greenberger |
| 5,614,503 A | | 3/1997 | Chaudhary et al. ....... 514/44 |
| 5,653,996 A | * | 8/1997 | Hsu ...................... 424/450 |
| 5,674,192 A | | 10/1997 | Sahatjian et al. |
| 5,702,384 A | | 12/1997 | Umeyama et al. |
| 5,705,151 A | | 1/1998 | Dow et al. |
| 5,736,145 A | * | 4/1998 | Cohen et al. ........... 424/194.11 |
| 5,744,335 A | | 4/1998 | Wolff et al. ............ 435/455 |
| 5,908,777 A | * | 6/1999 | Lee et al. .............. 435/320.1 |
| 5,912,236 A | | 6/1999 | Xu et al. |
| 6,051,429 A | * | 4/2000 | Hawley-Nelson et al. .. 435/458 |
| 6,124,270 A | | 9/2000 | Haensler |

FOREIGN PATENT DOCUMENTS

| | | | |
|---|---|---|---|
| EP | 0 335 133 | * | 3/1988 |
| EP | 0413957 A2 | * | 7/1990 |
| EP | 0 413 957 | * | 2/1991 |
| WO | WO 88/00824 | * | 2/1988 |
| WO | WO 88/03170 | * | 5/1988 |
| WO | WO 95/34647 | | 12/1995 |
| WO | WO 96/40958 | | 12/1996 |
| WO | WO 97/00965 | * | 1/1997 |
| WO | WO 97/04748 | * | 2/1997 |
| WO | W0 98/16201 | | 4/1998 |
| WO | WO 98/16202 | | 12/1998 |

OTHER PUBLICATIONS

Anderson et al., Human gene therapy, Nature, vol. 392, Apr. 30, 1998, pp. 25–30.*

Verma et al., Gene therepy–promises, probles and prospects, Nature, vol. 389, pp. 239–242, 1997.*

Bondeson et al., Promotion of acid–induced membrane fusion by basis pepties. Amino acid and phospholiped specificities, Biochimica et Biophysica Acta, vol. 1026, 1990, pp. 186–194.*

Goni et al., Surfoactant–Induced Lipsome fursion: Molecular Mechanisms and Biotechnological Applications, pp. 81–103, 1998.*

Tari et al., Biochemistry, 28, 7708–7712, 1989.*

Baatz, et al., "Utilization of Modified Surfactant–Associated Protein B for Delivery of DNA to Airway Cells in Culture," *Proc. Natl. Acad. Sci. USA*, 91:2547–2551, 1994.

Wimley, et al., "Experimentally Determined Hydrophobicity Scale for Proteins at Membrane Interfaces," *Nature Struc. Biol.*, 3:842–848 (1996).

Chelsky, et al., "Sequence Requirements for Synthetic Peptide–Mediated Translocation to the Nucleus," *Molecular and Cellular Biol.*, 9:2487–2492 (1989).

Gallay, et al., "HIV–1 Infection of Nondividing Cells: C–Terminal Tyrosine Phosphorylation of the Viral Matrix Protein is a Key Regulator," *Cell*, 80:379–388 (1995).

Collas, et al., "Rapid Targeting of the Plasmid DNA to Zebrafish Embryo Nuclei by the Nuclear Localization Signal of SV40 T Antigen," *Molecular Marine Biol. And Biotechn.*, 6(1):48–58 (1997).

Collas, et al., "Nuclear Localization Signal of SV40 T Antigen Directs Import of Plasmid DNA into Sea Urchin Male Pronuclei In Vitro," *Molecular Repro. and Develop.*, 45:431–438 (1996).

Longmuir, et al., 1992 ASBMB/Biophysical Society (Abstract).

Longmuir, et al., 1993 ASBMB/Biophysical Society (Abstract).

Bongartz et al., "Improved biological activity of antisense oligonucleotides conjugated to a fusogenic peptide," *Nucleic Acids Research*, 22(22):4681–4688 (1994).

Puyal et al., "Design of a short membrane–destabilizing peptide covalently bound to liposomes," *Biochimica et Biophysica Acta*, 1195:259–266 (1994).

* cited by examiner

*Primary Examiner*—Dave T. Nguyen
(74) *Attorney, Agent, or Firm*—Flehr Hohbach Test Albritton & Herbert LLP

(57) ABSTRACT

Described herein are liposome complexes and the individual components thereof for intracellular and/or intranuclear delivery of substances. Methods of use of the provided liposome complexes and components are also described. Generally, the liposome complexes described herein include a non-cationic lipid, a fusogenic peptide and a substance to be delivered to the cell and/or nucleus. In some of the liposome complexes described herein, the fusogenic peptide does not contain multiple positive charges at neutral pH and above. In these liposome complexes, two additional components are used in assembling the liposome complex with DNA.

40 Claims, 6 Drawing Sheets

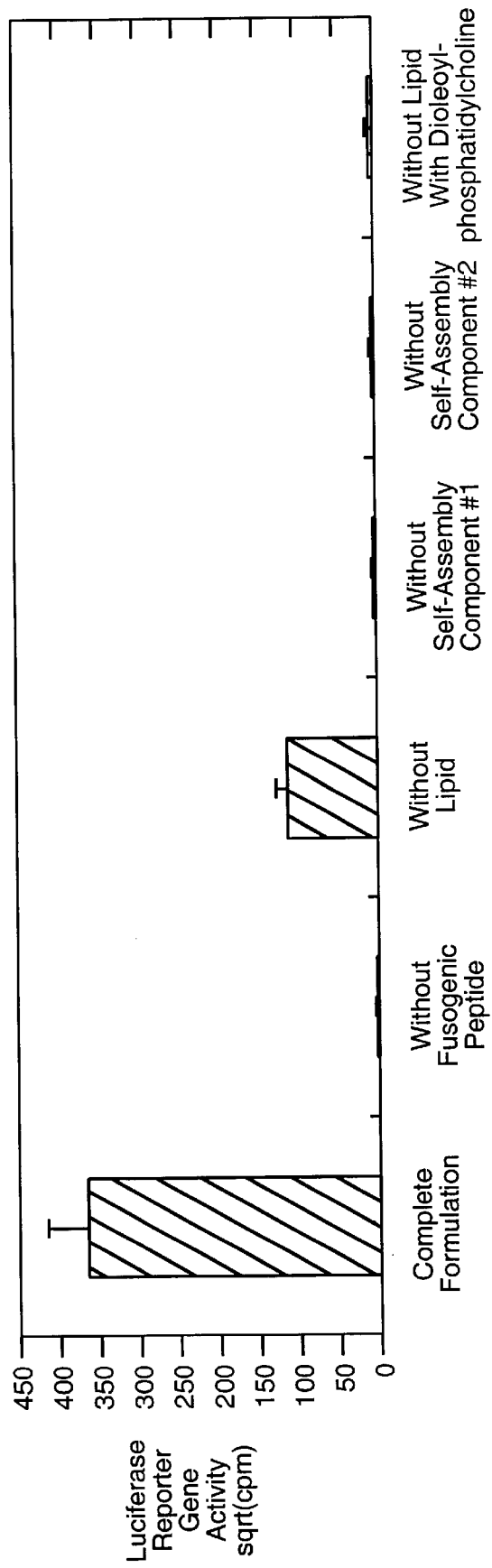
FIG._1

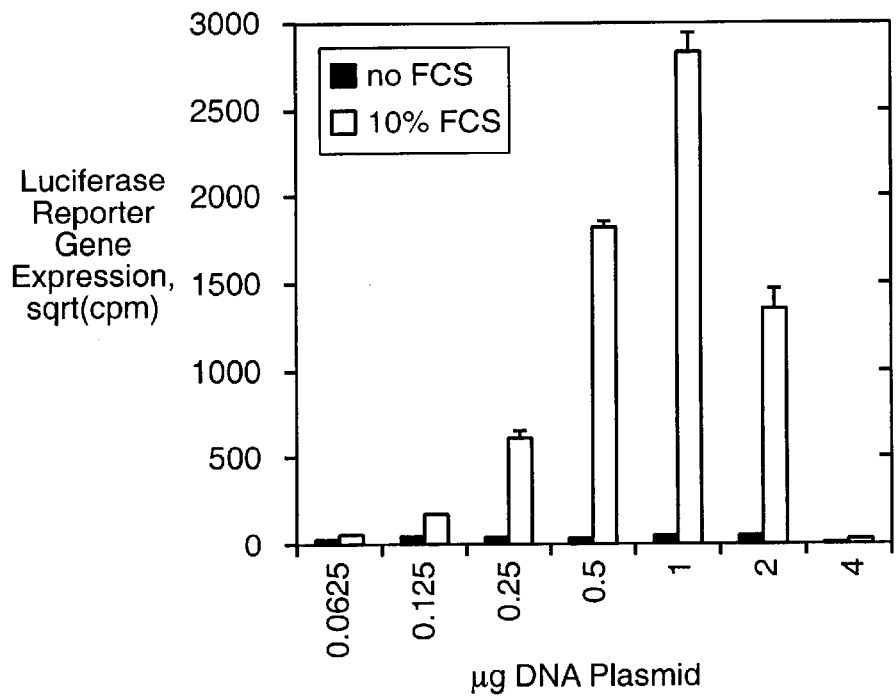
FIG._2
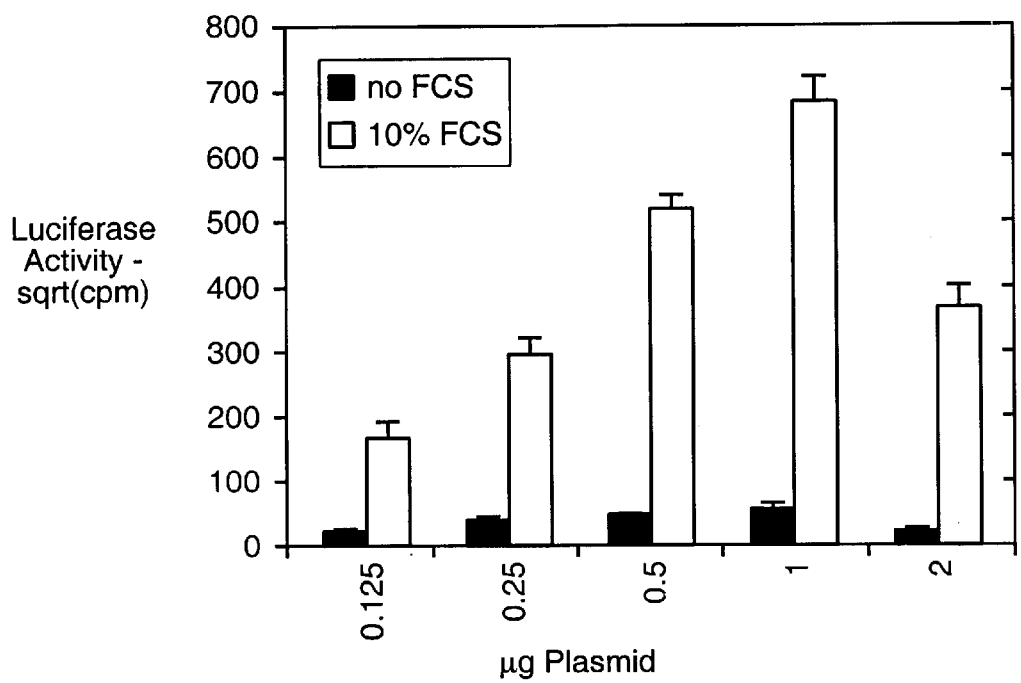
FIG._3

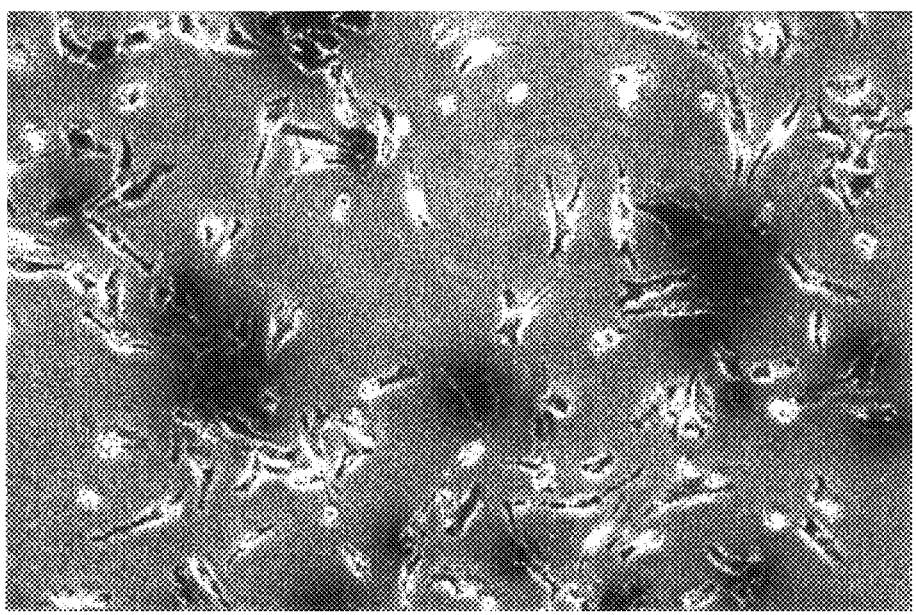
*FIG._4*
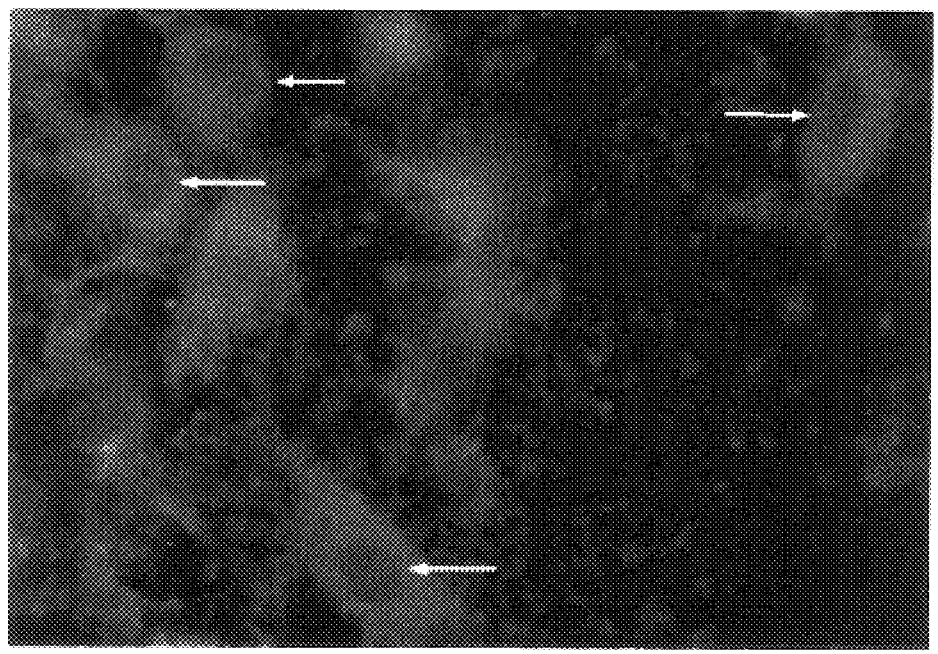
*FIG._6*

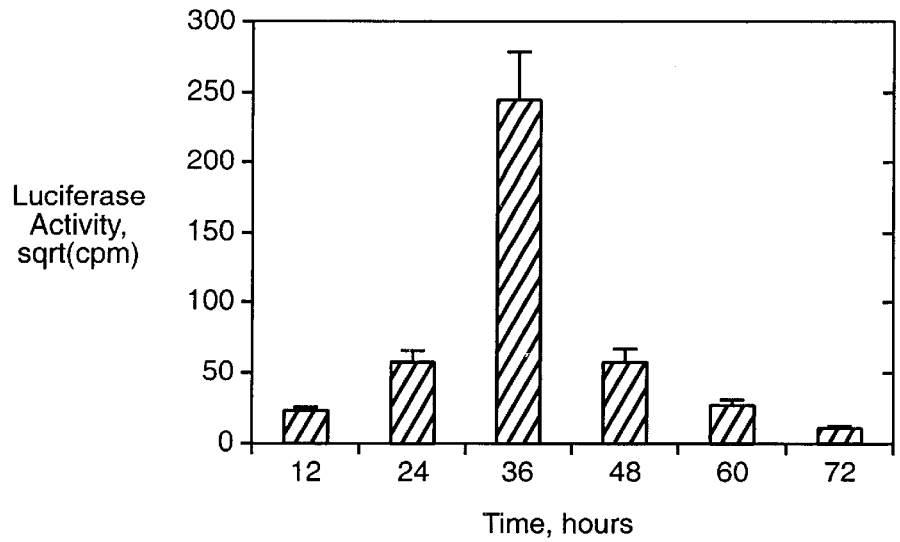
FIG._5
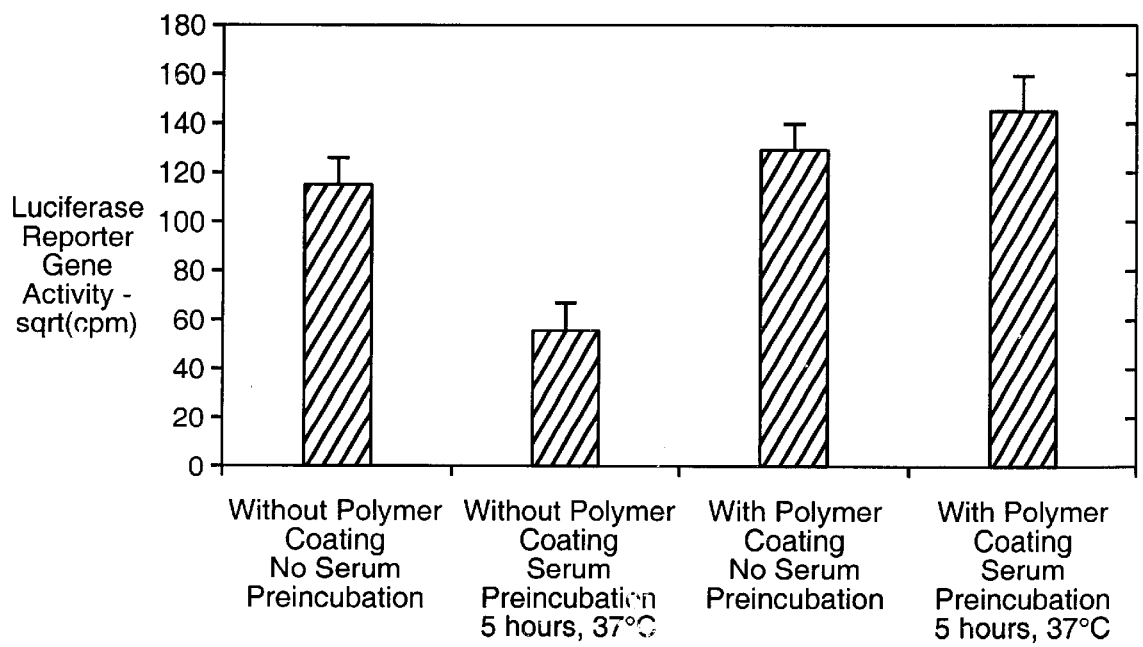
FIG._7

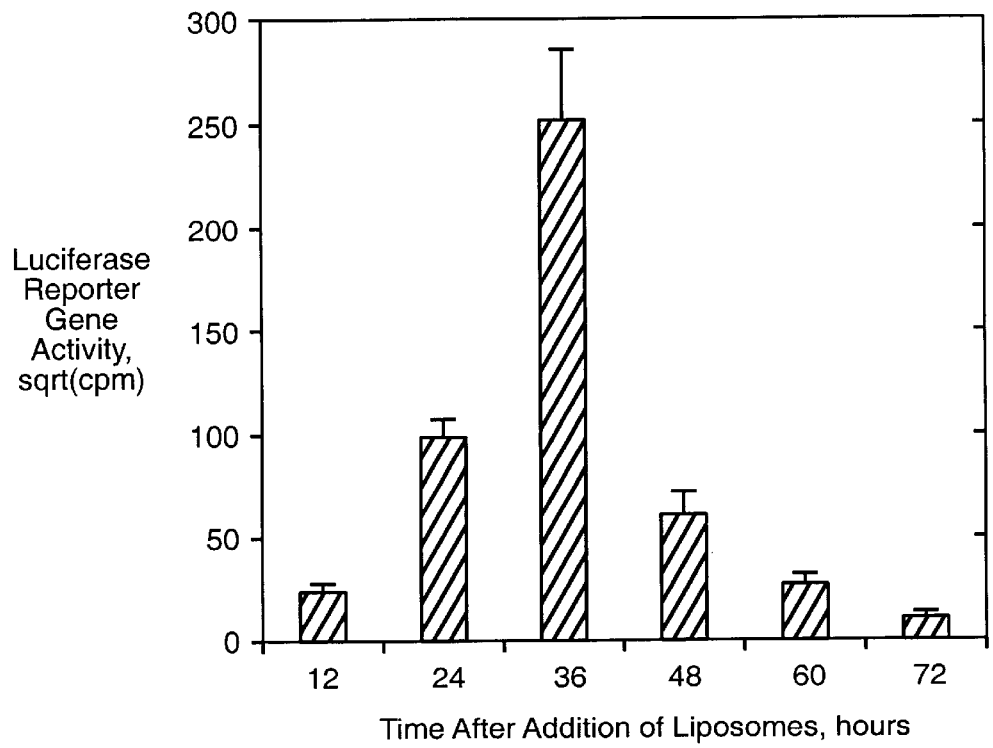
FIG._8A
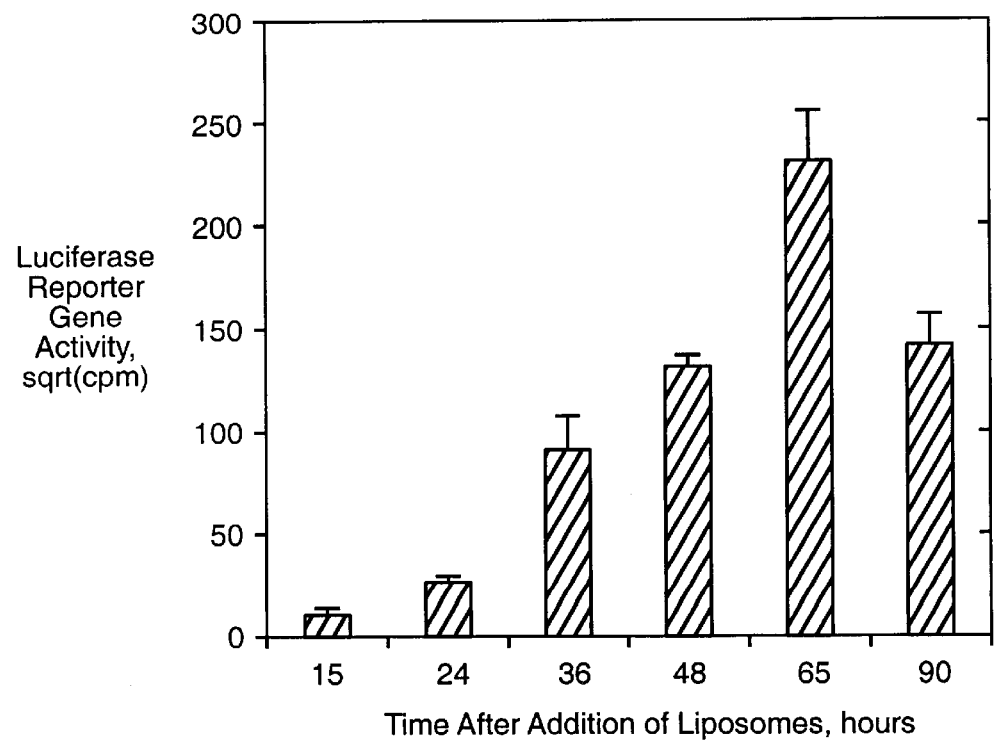
FIG._8B

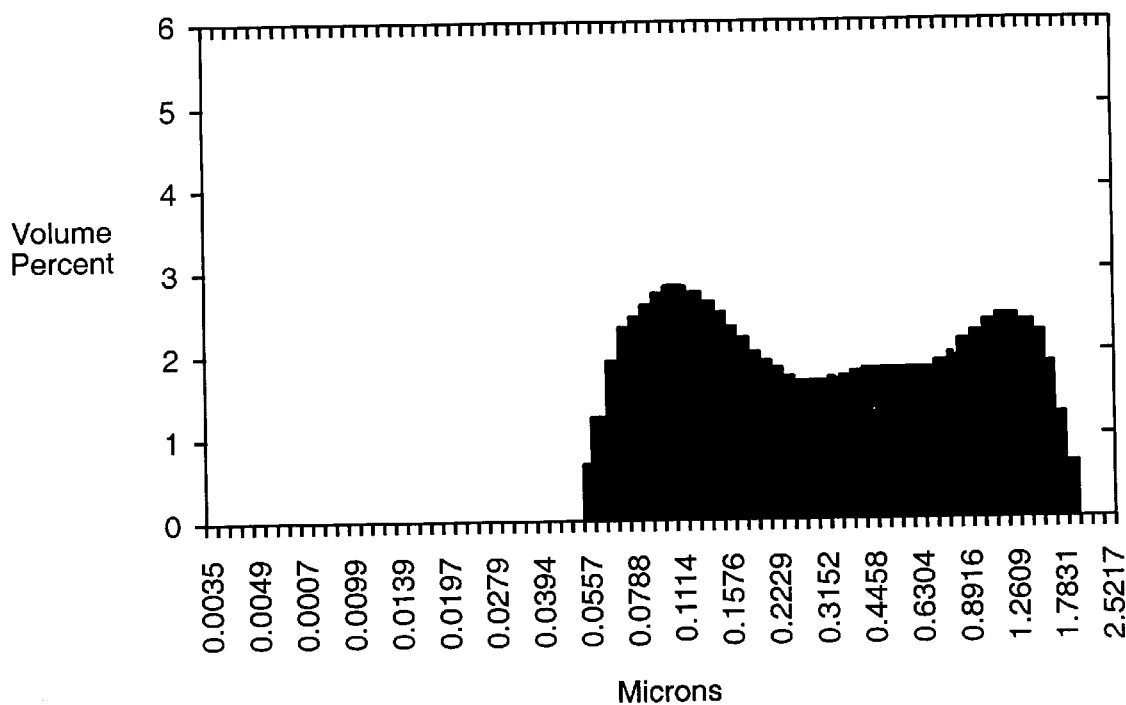
FIG._9A
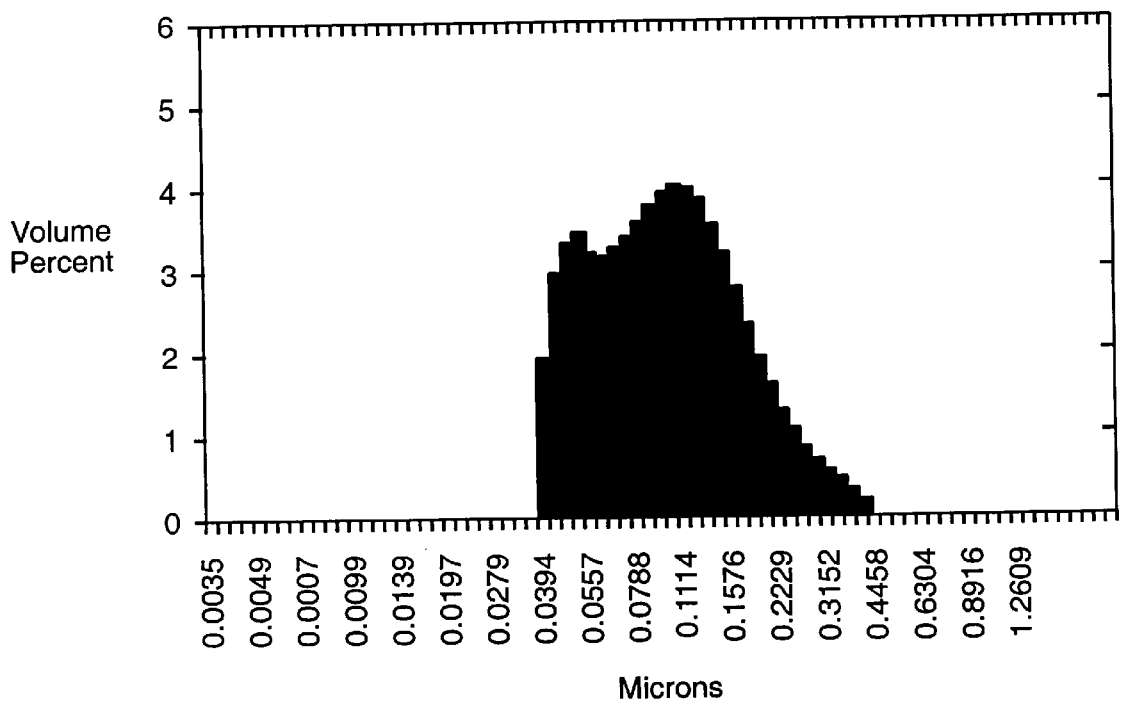
FIG._9B

LIPOSOME FUSION AND DELIVERY VEHICLE

FIELD OF THE INVENTION

The present invention is directed to a lipid based delivery vehicle. In particular, this invention is directed at cytoplasmic and/or nuclear delivery vehicles comprising a non-cationic lipid, a fusogenic peptide and a substance for delivery.

BACKGROUND OF THE INVENTION

Advances in cellular and molecular biology, particularly the identification of defective genes, has increased the need for efficient vehicles to deliver substances such as genes, antisense molecules, ribozymes, and various regulators and therapeutics both intracellularly and intranuclearly.

To date, delivery vehicles have included replication-defective adenoviral vectors, cationic liposomes and protein-cationic peptides. For example, one study reports a system to deliver DNA in vitro by covalently attaching the surfactant associated protein B (SP-B) to a 10 kDa polylysine. See, Baatz, J., et al., PNAS USA, 91:2547–2551 (1994). However, this study also reports that the transfection of cells is performed in serum-free medium and is most effective with the addition of adenovirus. Other studies report on the use of the N-terminal 25 amino acids of the SP-B for use in lipid mixing, but do not report on substance delivery or use with cell membranes. See, e.g., Longmuir, et al., 1992 ASBMB/Biophysical Society abstract; Longmuir, et al., 1993 Biophysical Society abstract.

It is therefore an object of the present invention to provide a delivery vehicle comprising a non-cationic lipid for cytoplasmic and/or nuclear delivery of substances wherein the vehicle is stable and can be used in biological extracellular fluids typically found in animals, particularly blood serum.

It is also an object of the present invention to provide a delivery vehicle for cytoplasmic and/or nuclear delivery comprising a fusogenic peptide. It is particularly an object to provide functional portions of fusogenic peptides, and variants thereof which are characterized by their ability to facilitate fusion between a cell membrane and a liposome comprising the fusogenic peptide. It is also an object to provide fusogenic peptides which are characterized by their ability to facilitate transfer of substances across cellular membranes. It is also an object to provide variants of fusogenic peptides which exhibit lower cytotoxicity than the corresponding native fusogenic peptide.

It is also an object of the present invention to provide methods for assembling the aforementioned delivery vehicles as well as to provide the components used therein. It is further an object to provide methods for use of said delivery vehicles.

SUMMARY OF THE INVENTION

In accordance with the foregoing objectives, provided herein are liposome complexes and the components thereof for use in cytoplasmic and/or nuclear delivery of substances. Methods of making and using such liposome complexes are also provided. In one of the embodiments, components of the liposome complex include a non-cationic lipid and a fusogenic peptide. In some embodiments, the liposome complex further includes a substance to be delivered to the cytoplasm and/or nucleus.

The fusogenic peptides of the invention are characterized by their ability to facilitate fusion between a cell membrane and a liposome comprising the fusogenic peptide. Such peptides are also characterized by their ability to facilitate transfer of substances across cell membranes, particularly eukaryotic cell membranes. In a preferred embodiment, the fusogenic peptide comprises the consensus sequence: X-H-XXHHX-H-X-H (SEQ ID NO: 7).

In the consensus sequence, SEQ ID NO:7, "X" is any naturally occuring or synthetic hydrophobic amino acid. Examples of hydrophobic amino acids include alanine (Ala), valine (Val), isoleucine (Ile), leucine (Leu), norleucine (NorLeu), and phenylalanine (Phe). It is understood that variant or modified amino acids which retain or are altered to have hydrophobicity can be utilized. Further in the consensus sequence, at least 3 of the "H" positions are occupied by any naturally occuring or synthetic amino acid having a pKa of about 5 to about 7, and preferably about 6, wherein any remaining "H" positions are occupied by any amino acid, preferably a hydrophilic amino acid. Examples of amino acids having a suitable pKa include histidine, 1-methyl-histidine and 3-methyl histidine. Still further in the consensus sequence, "-" is any amino acid. Other embodiments include peptides derived from the pulmonary surfactant protein B (SP-B).

The non-cationic lipids provided herein are characterized by their ability to complex stably with fusogenic peptides and substance(s) to be delivered across cell membranes in the presence of biological fluids such as blood serum. Embodiments of such non-cationic lipids include 1,2-dimyristoleoyl--sn-glycero-3-phosphocholine (14:1-PC), and 1,2-dilauroyl-sn-glycero-3-phosphocholine (12:0-PC).

Any substance which can potentially modify the genotype or phenotype of the cell can be delivered according to the invention. Examples of substances to be delivered include genes, RNA, oligonucleotides, antisense molecules, ribozymes, peptides, factors and various regulators and therapeutics. In a preferred embodiment, when the substance is to be delivered to the inside of the nucleus, a nuclear localization signal peptide is also included.

The fusogenic peptides of the invention at physiological pH generally have a net positive charge. However, in some of the embodiments provided herein, the fusogenic peptide does not contain multiple positive charges at neutral pH and above. In such embodiments, and when the substance to be delivered is a negatively charged polymer such as DNA or RNA, additional components are preferably used in assembling the liposome complex. For example, in one embodiment, a positively charged companion peptide such as a nuclear localization signal peptide (NLSP) reacted with N-iodoacetyl-(1,2-dioleoyl)-sn-glycero-3-phosphoethanolamine (N-iodoacetyl-DOPE) or N-(3-maleimido)benzoyl-DOPE (DOPE-MBS) is additionally utilized.

BRIEF DESCRIPTION OF THE DRAWINGS

FIG. 1 is a bar graph indicating reporter gene expression as the result of omitting components of liposome formulations. Component #1 is N-iodoacetyl-DOPE and component #2 is a NLSP (SEQ ID NO:4).

FIG. 2 is a bar graph indicating reporter gene expression when different levels of the liposome complex in accordance with the present invention are added to HeLa Cells in the presence and absence of 10% serum. The 10% FCS bar is the taller bar in each pair of bars.

FIG. 3 is a bar graph indicating reporter gene expression when different levels of a liposome complex in accordance with the present invention are added to NIH 3T3 cells in the presence and absence of 10% serum. The 10% FCS bar is the taller bar in each pair of bars.

FIG. 4 is a photograph of HeLa cells transfected with reporter gene using liposome complexes in accordance with the present invention in the presence of 10% serum.

FIG. 5 is a bar graph which shows the time course of luciferase gene expression, when delivered to cells by a liposome complex in accordance with the present invention.

FIG. 6 is a photograph showing the delivery of fluorescently labeled dextran to the cell cytoplasm by use of a liposome complex in accordance with the present invention.

FIG. 7 is a bar graph showing reporter gene expression levels when the liposome complexes in accordance with the present invention are preincubated or not in serum and when they are used with and without polymer coating.

FIGS. 8A and 8B are bar graphs showing the time course of transfection from liposome complexes in accordance with the present invention with (FIG. 8B) and without (FIG. 8A) polymer coating.

FIGS. 9A and 9B are graphs which show particle size distribution of liposomes without (FIG. 9A) and with (FIG. 9B) polymer coating.

DETAILED DESCRIPTION OF THE INVENTION

The fusogenic peptides provided herein have the ability to facilitate fusion between a liposome complex comprising non-cationic lipids and the fusogenic peptide, and a cell membrane. After fusion, the fusogenic peptide facilitates the transfer of the lipid complex across the cell membrane. In preferred embodiments, the cell membrane is an eukaryotic cell membrane. In general, the rate and/or extent of fusion and transfer will be greater for a lipid complex comprising the fusogenic peptide as compared to the same complex without the fusogenic peptide. In a preferred embodiment, the liposome complex further comprises a substance to be delivered.

Suitable fusogenic peptides include peptides based upon the sequence of the processed form of the protein pulmonary surfactant B (SP-B), preferably from human. In one embodiment, the peptide comprises the N-terminus of SP-B. The N-terminus of SP-B is defined herein as being approximately the first 25 amino acids from the N-terminus. The sequence of this peptide as found in nature is as follows:

N-terminus-Phe-Pro-Ile-Pro-Leu-Pro-Tyr-Cys-Trp-Leu-Cys-Arg-Ala-Leu-Ile-Lys-Arg-Ile-Gln-Ala-Met-Ile-Pro-Lys-Gly-C-terminus (SEQ ID NO: 1).

In a preferred embodiment, the fusogenic peptide consists essentially of the N-terminus of SP-B.

In another embodiment, the fusogenic peptide is a variant of an N-terminal SP-B peptide wherein the variant also has the ability to facilitate fusion between a liposome complex comprising the fusogenic peptide and a cell membrane, as well as facilitate transfer of the liposome complex and its contents across the cell membrane. Examples of variant N-terminal SP-B peptides include peptides having one or more of the following changes to the native N-terminal sequence (SEQ ID NO:1):

1) substitution of one or more of the lysines and/or arginines of the hydrophilic stripe of the amphipathic alpha helix with histidine;
2) substitution of one or more of the hydrophobic amino acids leucines and isoleucines from positions 10 to 25 (the hydrophobic stripe of the amphipathic alpha helix) with norleucine;
3) substitution of at least one of the cysteine amino acids with alanine, preferably at either position 8 and/or position 11;
4) lengthening the membrane anchoring sequence at positions 1–6 of SEQ ID NO: 1, preferably by inserting at least I to 6 pairs of Ile-Pro or Leu-Pro, or a combination thereof, after position 2, 4 or 6 of SEQ ID NO: 1; and
5) replacing the C-terminus carboxylic acid group of the peptide with an amide group.

In preferred embodiments, the variant N-terminal SP-B peptides exhibit lower cytotoxicity and/or greater membrane/liposome complex fusion and delivery efficacy than the native N-terminal SP-B peptides. Two examples of variant N-terminal SP-B peptides are as follows:

Phe-Pro-Ile-Pro-Leu-Pro-Ile-Pro-Leu-Pro-Ile-Pro-Try-Cys-Trp-Leu-Ala-His-Ala-Leu-Ile-His-His-Ile-Gln-Ala-Met-Ile-Pro-His-Gly-amide (SEQ ID NO: 2); and Phe-Pro-Ile-Pro-Leu-Pro-Ile-Pro-Leu-Pro-Ile-Pro-Try-Cys-Trp-Norleu-Ala-His-Ala-Norleu-Norleu-His-His-Norleu-Gln-Ala-Met-Norleu-Pro-His-Gly-amide (SEQ ID NO: 3).

In another embodiment, the fusogenic peptide comprises the following consensus amino acid sequence:
X-H-XXHHX-H-X-H (SEQ ID NO: 7).

In the consensus sequence, "X" is any naturally occuring or synthetic hydrophobic amino acid. Examples of hydrophobic amino acids include alanine (Ala), valine (Val), isoleucine (Ile), leucine (Leu), norleucine (NorLeu), and phenylalanine (Phe). It is understood that variant or modified amino acids which retain or are altered to have hydrophobicity can be utilized. The experimental determination of hydrophobicity is further described in Wimley and White, *Nat. Struc. Biol.*, 3(10):842–848 (1996). Generally, a hydrophobic amino acid has a positive free energy of transfer from a lipid environment to an aqueous environment. Further in the consensus sequence, at least 3 of the "H" positions are occupied by any naturally occuring or synthetic amino acid having a pKa of about 5 to about 7, and preferably about 6. Examples of amino acids having such a pKa include histidine, 1-methyl-histidine and 3-methyl histidine. Where there are any remaining "H" positions not occupied with an amino acid having a pKa from about 5 to about 7, these positions are occupied by any amino acid, or preferably, hydrophilic amino acid(s). Still further in the consensus sequence, "-" is any amino acid.

Given the consensus sequence and the description of the amino acids provided herein, the skilled artisan can routinely form a variety of peptides. For example, according to the descriptions provided herein, the peptide of SEQ ID NO:7 can be any of the following peptides:

Leu-Ala-His-Ala-Leu-Leu-His-His-Leu-Ala-His-Ala-Leu-Ala-His (SEQ ID NO:8);

Ile-Ala-His-Ala-Ile-Ile-His-His-Ile-Ala-His-Ala-Ile-Ala-His (SEQ ID NO:9);

Leu-Ala-His-Ala-Ile-Leu-His-His-Ile-Ala-His-Ala-Leu-Ala-His (SEQ ID NO:10);

Phe-Ala-His-Ala-Phe-Phe-His-His-Phe-Ala-His-Ala-Phe-Ala-His (SEQ ID NO:11);

Leu-Leu-His-Leu-Leu-Leu-His-His-Leu-Leu-His-Leu-Leu-Leu-His (SEQ ID NO:12);

Leu-Ala-His-Ala-Leu-Leu-Ser-His-Leu-Ala-His-Ala-Leu-Ala-Ser (SEQ ID NO:13);

Leu-Ala-His-Ala-Leu-Leu-Glu-His-Leu-Ala-Glu-Ala-Leu-Ala-His (SEQ ID NO:14); and

Leu-Ser-His-Ser-Leu-Leu-His-His-Leu-Ser-His-Ser-Leu-Ser-His (SEQ ID NO:15).

In a preferred embodiment, the consensus sequence is attached to any membrane anchoring peptide. Membrane anchoring peptides are well known in the art. Examples of a membrane anchoring peptide include the amino acid sequences set forth in amino acids 1 through 6, 7, 8, 9 or 10 in SEQ ID NO:1 and the amino acid sequence set forth in SEQ ID NO:2, amino acids 1–15.

In one embodiment, the fusogenic peptide consists essentially of the peptide having the sequence of amino acids 1 through 6, 7, 8, 9 or 10 of SEQ ID NO:1 followed by any one of SEQ ID NO:7 through SEQ ID NO:15. In still another embodiment, the fusogenic peptide consists essentially of the peptide having the sequence of amino acids 1 through 15 of SEQ ID NO:2 followed by any one of SEQ ID NO:7 through SEQ ID NO:15.

All of the fusogenic peptides described herein can be modified. Preferred modifications provide improved delivery efficiency and/or reduced cytoxicity over the corresponding non-modified forms. In preferred embodiments, the modifications change the net charge of the fusogenic peptide at neutral pH. Examples of preferred modifications include:

1) wherein the fusogenic peptide has a positive charge at the N-terminus, this charge is changed to be a neutral or negative charge. This can be done by previously described methods such as acetylating the N-terminus with the N-hydroxysuccinimide ester of acetic acid or by reacting the N-terminus with succinic anhydride;

2) wherein the fusogenic peptide comprises cysteine, adding a negative charge on the —SH group of cysteine. This can be done by previously described methods such as reacting the —SH group of a cysteine with iodoacetic acid; and/or 3) wherein the fusogenic peptide comprises cysteine, conjugating polyethylene glycol to the —SH group of cysteine via a disulfide linkage by methods previously described.

The fusogenic peptides can be made by standard automated peptide synthesis. The peptide is cleaved by standard techniques using trifluoroacetic acid (10 ml), water (0.5 ml), ethanedithiol (0.25 ml), and thioanisole (0.25 ml) (per gram of peptide-containing resin). The peptide (approximately 200 mg) is precipitated in 60 ml cold tert-butyl methyl ether, washed three times with cold tert-butyl methyl ether, redissolved in 10 ml of 1 mM hydrochloric acid, and lyophilized.

Alternatively, the fusogenic peptides are made by expression of nucleic acids encoding the fusogenic peptides. The nucleic acids encoding the fusogenic peptides are within the scope of the invention. The nucleic acids can be naturally occuring and isolated, recombinately formed or chemically synthesized, i.e. by oligonuleotide synthesis. The amino acid sequences of the fusogenic peptides are provided and are generally relatively short, therefore, the codons encoding the desired sequence can be routinely selected.

For purification of the fusogenic peptides, approximately 10 mg of peptide are dissolved in 0.5 ml of 3/2 (water+0.1% trifluoroacetic acid (TFA))/(acetonitrile+0.1% TFA), and chromatographed by HPLC on an RP-3 column (Hamilton) in a gradient from 100% water+0.1% TFA to 40/60 (water+0.1% TFA)/(acetonitrile+0.1% TFA). The first major component off the column is taken as the purified peptide. Components which elute afterwards appear to be peptide where the amino acid protecting groups (essential during peptide synthesis) have not been completely removed. Correct identity of the peptide is confirmed by mass spectroscopy.

Samples are stored at −70° C. in the same solvent. Samples are quantitated by 1) absorbency of the tryptophan+tyrosine amino acids at 280 nm wavelength, and 2) absorbency at 410 nm after reaction of the cysteine group with 5,5'-dithio-bis(2-nitrobenzoic acid) (DTNB, or Ellman's reagent).

The non-cationic lipids provided herein, in combination with the fusogenic peptides and the substance(s) to be delivered, result in detectable liposome-cell fusion and delivery of the substance(s) contained therein and are effective in biological fluids including blood serum. The preferred non-cationic lipid is a zwitterionic, neutral, or anionic phospholipid with 2 fatty acid chains. The fatty acid chains can be 2 unsaturated fatty acid chains having a length of 14 carbons or shorter, or 2 saturated fatty acid chains having a length of 14 carbons or shorter. In another embodiment, the non-cationic lipid has one unsaturated fatty acid chain having a length of 14 carbons or shorter and one saturated fatty acid chain having a length of 14 carbons or shorter. The number of carbons is preferably 8, 9, 10, 11, 12, 13 or 14. In preferred embodiments, the number of carbons in the fatty acid chains is either 12 or 14. Two embodiments of the non-cationic lipids provided herein are 1,2-dimyristoleoyl-sn-glycero-3-phosphocholine (abbreviated 14:1-PC) and 1,2-dilauroyl-sn-glycero-3-phosphocholine (abbreviated 12:0-PC).

Lipids similar to 14:1-PC and 12:0-PC can also be used. These include phosphatidylcholines with fatty acids having a length of 14 carbons or shorter, preferably 8–14 carbons, with or without one or more cis or trans double bonds anywhere on the fatty acid chain. Other lipid classes with fatty acids having a length of 14-carbons or shorter, preferably 8–14, can also be used. These include the phosphatidylethanolamines, the phosphatidylserines, the phosphatidylinositols and other members of this family. Examples also include phosphatidylglycerols, phosphatidic acids, diacylglycerols, sphingolipids and derivatives thereof including formulations wherein an acyl linkage is replaced by an ether linkage as in alkyl lipids.

In one of the embodiments provided herein, the fusogenic peptide does not contain multiple positive charges at neutral pH and above. An example of this embodiment is when at least three of the lysine and arginine residues of the fusogenic peptide derived from the N-terminus of SP-B are replaced with histidine. Since the pKa of histidine is approximately 6.1, and therefore, primarily uncharged above pH 7. Thus, the presence of histidine effectively reduces the amount of positive charge on the fusogenic peptide.

In embodiments wherein the fusogenic peptide does not contain multiple positive charges at neutral pH and above and wherein the substance to be delivered is negatively charged, such as DNA, a positively charged "companion peptide" is used to facilitate assembly. In preferred embodiments, the positively charged companion peptide is a nuclear localization signal peptide.

In one of the embodiments, the positively charged companion is attached to a lipid to form a peptide-lipid conjugate. The peptide-lipid conjugate is able to complex with the liposome complex described herein. For example, in one of the embodiments, the positively charged companion peptide has at least one cysteine for cross-linking to the lipid.

In preferred embodiments, the peptide-lipid conjugate is formed by coupling the positively charged companion peptide to cross-linking phoshatidylethanolamines. For example, N-iodoacetyl-( 1 ,2-dioleoyl)-sn-glycero-3-phosphoethanolamine (N-iodoacetyl-DOPE) can be utilized. Other iodoacetyl linkages can be used to form, for example: N-iodoacetyl-(1,2-dinervonoyl)-sn-glycero-3-phosphoethanolamine; N-iodoacetyl-(1,2-palmitoyl)-snglycero-3-phosphoethanolamine; and N-iodoacetyl-(1,2-O-hexadecyl)-sn-glycero-3-phosphoethanolamine.

N-iodoacetyl-DOPE can be obtained by the reaction of 1,2-dioleoyl-sn-glycero-3-phosphoethanolamine (also called dioleoylphosphatidylethanolamine, or DOPE) with the N-hydroxysuccinimide (NHS) ester of iodoacetic acid. The DOPE is obtained commercially from Avanti Polar Lipids, used without purification, stored in chloroform solution at −70° C., and quantitated by phosphate analysis. The NHS ester of iodoacetic acid is obtained from Sigma Chemical Company (St. Louis, Mo.), stored at −20° C., and used without further purification. The two compounds are combined by reacting 20 $\mu$mol DOPE with 30 $\mu$mol iodoacetic acid NHS ester in 1.5 ml of 2/1 chloroform/methanol+10 $\mu$l triethylamine at room temperature for 1 hour. Afterwards, 10 $\mu$l of acetic acid are added, and the solvents are evaporated with a stream of $N_2$ gas. The residue is redissolved in distilled 95% ethanol and purified on a column of LH-20 Sephadex. The product of the reaction is N-iodoacetyl-DOPE. The product is stored in chloroform solution at −70° C., and quantitated by phosphate analysis.

In an alternative embodiment, the positively charged companion peptide is coupled to 3-maleimidobenzoic acid N-hydroxysuccinimide ester (MBS) available from Sigma Chemical Company. The DOPE-MBS conjugate can be formed as follows. 15 micromoles of MBS is dissolved in 0.5 ml chloroform and added to a solution of DOPE, 10 micromoles in 1 ml chloroform. 25 microliters of triethylamine is then added. This mixture is reacted for 1 hour at room temperature. 25 microliters of acetic acid is then added. The chloroform is washed twice with 2–3 milliliters water and allowed to evaporate. The remainder is redissolved in 1 ml ethanol/chloroform (3:1 v/v) and purified by chromatography on LH-20 Sephadex in 3:1 ethanol/chloroform (v/v). It can be quantitated by phosphate analysis.

When delivery into the nucleus is desired, the positively charged companion peptide is preferably a nuclear localization signal peptide. Nuclear localization signal peptides known in the art as well as novel nuclear localization signal peptides described herein can be used in the system provided herein.

Examples of suitable known nuclear localization signal peptides include: (1) a peptide based upon polyomavirus large T antigen, CGYGVSRKRPRPG-amide (SEQ ID NO:4) (Chelsky, et al., *Molec. Cellular Biol.*, 9: 2487–2492 (1989) and (2) a peptide based upon a sequence found in HIV-1 matrix protein, CGKKKYKLKH-amide (SEQ ID NO:5) (Gallay, et al., *Cell*, 80: 379–388 (1995).

A novel nuclear localization peptide provided herein has a second cysteine added to the peptide of SEQ ID NO:5 for improved stability and is CGCGKKKYKLKH-amide (SEQ ID NO:6). In preferred embodiments, the nuclear localization signal has at least one cysteine for cross-linking to a lipid. Further compositions and methods for use in the present invention when nuclear localization is desired are described in PCT application no. PCT/US95/07543, Collas and Alestrom, *Mol. Mar. Biol. and Biotech.*, 6(1):48–58 (1997) and Collas and Alestrom, *Mol. Reprod. and Dev.*, 45:431–438 (1996).

Each of the peptides can be made by automated peptide synthesis. The synthesis, cleavage, HPLC purification, storage, and quantitative analysis of these peptides are carried out as described above for the fusogenic peptides.

A wide variety of substances can be delivered by the system described herein. Any pharmaceutical or therapeutic can be delivered. Any substance which may modify the genotype or phenotype of the cell may be delivered. For example, nucleic acids which are single or double stranded up to at least 30 kb can be delivered. Peptides, factors, antisense molecules, and transcription regulators can also be delivered. Examples of commercially-available DNA plasmids are: (1) pGL3-control vector with a luciferase reporter gene available from Promega (Madison, Wis.); and (2) pCMVβ plasmid with the β-galactosidase reporter gene available from ClonTech (Palo Alto, Calif.). However, any nucleic acids known in the art can be used in the system described herein.

The plasmids are maintained in *E. coli* bacteria and purified using commercially-available kits and protocols from QIAGEN (Chatsworth, Calif.). The plasmids are stored in TE buffer (10 mM Tris-HCl+1 mM EDTA, pH 8.0)

In an embodiment provided herein, the liposome complexes are modified by attaching nonproteinacious polymers, e.g., polyethylene glycol, polypropylene glycol or polyoxyalkylenes, thereto for stabilizing and prolonging the circulation time of the liposome complexes when injected in vivo in comparison to liposome complexes not having this modification. In one embodiment, polyethylene glycol is used. The polyethylene glycol is attached to the fusogenic peptide via an —SH group of cysteine of the fusogenic peptide. Suitable polyethylene glycols include methoxy-polyethylene glycol of 500 MW to 500,000 MW, and preferably, 5,000 MW. The linkage preferred is a disulfide bond (—S—S—).

The polyethylene glycol, or other polymer glycol, attached to the fusogenic peptide by this method, does not block the fusion activity of the liposome. It is believed that this is because the —S—S—bond is broken by enzymatic activity upon uptake of the fusogenic liposome by cells in culture. In preferred embodiments, the polyethylene glycol is attached to DOPE. Methods and compositions related to polymer coatings for liposomes are further described in Kirpotin, et al., *FEBS letters*, 388:115–118 (1996).

Ligands for cell targeting are optionally added to the liposome complexes described herein to assist in cell targeting. Preferred ligands specifically bind to the target. For example, asialofetuin, linked to phosphatidylethanolamine, can be added to the liposome complexes. This complex targets the asialoglycoprotein receptor of HepG2 liver cells. Other examples include covalently linking folic acid to the liposome complex to target the folate receptor of killer B cells and covalently linking transferrin to target the transferrin receptor present on most cells.

Generally, any antibody, receptor ligand component can be used which is known to target specific cell types, including injured, diseased and cancerous cells. In a preferred embodiment, growth factor receptors known to have increased expression in tumors are targeted. For example, the ligands for cell targeting include monoclonal antibodies or portions thereof which bind to the EGF receptor, the p97 (transferrin) receptor, and to the IL-2 receptor.

In an embodiment which includes a ligand for cell targeting, the following procedures can be used. First, a cross-linking phosphatidylethanolamine with a disulfide linkage is made. DOPE is reacted with a five-fold excess of the homobifunctional cross-linking reagent DTSP (3,3'-dithio-bis(proprionic acid N-hydroxysuccinimide ester)) in chloroform in the presence of triethylamine. The resulting conjugate is then purified by LH-20 Sephadex chromatography. This conjugate will react with free amino groups of targeting ligands when carried out in a detergent solution (100 mM cholate, 10 mM borate buffer, pH 9.2) for several hours at room temperature. This solution is then mixed with the remainder of the liposome components prior to dialysis.

In general, the appropriate quantities for administration to humans can be assessed by the data provided in the specific examples below. In an embodiment provided herein, a pharmaceutically acceptable carrier is used with administration of the liposome complexes. The liposome complexes provided herein can be directly injected into the tissue or organ. Alternatively, cells can be taken from a patient, treated and replaced in the patient. The liposome complexes provided herein can be used as vehicles for gene therapy. The system provided herein can effectively treat any disease which requires for effective treatment, delivery of a substance intracellularly and/or intranuclearly, which can be delivered by the system described herein. In particular, tumors can be treated, as well as organs having cells missing a required function, such as in diabetes patients.

The invention also includes kits having each of or a combination of the components of the liposome complex described herein, including appropriate buffers and devices for assembly and administration. For example, the kit can include centrifuge tubes and racks for assembly as well as syringes.

The following examples are intended merely to illustrate embodiments of the invention and are not to be considered as limited to the details of each example.

SPECIFIC EXAMPLE 1

Assembly of a Liposome Complex

Example A

The following procedure is used to produce fusogenic liposomes containing 12 µg DNA plasmid in approximately 1 ml of solution. The quantities below are for a 1 ml final solution. The amounts of the components can vary depending on the result which is desired. Step 1(i) or 1(ii) is not included when DNA, RNA or another negatively charged polymer is not the substance to be delivered. Additionally, the steps do not need to take place in the following order.

1(i). Reaction of N-iodoacetyl-DOPE with Nuclear Localization Signal Peptide

A solution of 40 nmol of nuclear localization signal peptide is placed in a 12×75 culture tube and the solvents evaporated with $N_2$ gas. A solution of 160 nmol of N-iodoacetyl-DOPE is placed in a separate culture tube and the solvents evaporated. The N-iodoacetyl-DOPE is dissolved in 50 µl dimethylformamide and transferred to the tube with the nuclear localization signal peptide. The components are allowed to react for 34 hours at room temperature. Then, 0.5 ml of a solution of 250 mM sodium cholate in PB buffer (1.5 mM $KH_2PO_4$+8.1 mM $Na_2HPO_4$, pH 7.4) is added. Alternative detergents can be used. Examples include bile salts such as cholate, deoxycholate and taurocholate. The buffer can also contain various salt solutions up to 50 mM. Afterwards, 5 µl of beta-mercaptoethanol is added to react with the excess N-iodoacetyl-DOPE.

Preferred ranges of the components are: nuclear localization signal peptide, 10 nmol to 200 nmol; and N-iodoacetyl-DOPE, 102 nmol to 400 nmol. The optimal amounts of these components may vary depending upon (a) the target; (b) the amount of fusogenic peptide in the final formulation; and (c) the net charge on the fusogenic peptide.

This procedure is used when the nuclear localization signal peptide (or other positively charged composition) plus the N-iodoacetyl DOPE (or other cross-linking lipid) are used immediately for liposome formation. In a separate embodiment, after the 3–4 hours reaction in dimethylformamide, the lipid-peptide conjugate is precipitated with 5 ml of tert-butyl methyl ether. The precipitate is centrifuged a 1000×g, and the supernatant with the excess (unreacted) lipid is discarded. The precipitate, containing lipid-peptide conjugate without excess lipid, is redissolved in dimethylsulfoxide and stored at −20 degrees C. until further use. When used for liposome formation, the lipid-peptide conjugate in dimethylsulfoxide is added directly to the solution of 250 mM cholate in PB buffer.

1(ii). DOPE-MBS with Nuclear Localization Signal Peptide

A nuclear localization signal peptide-lipid conjugate can also be prepared as follows:

The following reagents are used:

Dioleoylphosphatidylethanolamine (DOPE), approximately 10 micromoles per milliliter in chloroform; 3-Maleimidobenzoic acid N-hydroxysuccinimide ester (MBS), dry powder; Nuclear localization signal peptide (SEQ ID NO: 5) in acetonitrile/water/trifluoroacetic acid 50:50:0.1 (v/v/v).

Take 10 micromoles of DOPE (in 1 ml chloroform). Dissolve 15 micromoles of MBS in 0.5 ml chloroform. Add to solution of DOPE. Add 25 microliters of triethylamine. Let react 1 hour at room temperature. Add 25 microliters acetic acid. Wash chloroform twice with 2–3 milliliters water. Evaporate chloroform.

Redissolve in 1 ml ethanol/chloroform (3:1 v/v). Purify by chromatography on LH-20 Sephadex in 3:1 ethanol/chloroform (v/v). Quantitate by phosphate analysis.

Preparation of the lipid-peptide conjugate is as follows. Take 1 micromole of nuclear localization signal peptide and place in a 16×100 screw-cap test tube. Evaporate to dryness with nitrogen gas. In a separate tube place 2 micromoles of DOPE-MBS conjugate. Evaporate solvent. Dissolve DOPE-MBS conjugate in 200 microliters of dimethylformamide. Transfer to the tube containing the peptide and allow to react for 1 hour at room temperature. Evaporate dimethylformamide with nitrogen gas. Add 50 microliters dimethylsulfoxide. Precipitate the lipid-peptide conjugate with the addition of five milliliters of tert-butyl methyl ether. Centrifuge at 1000×g for 5 min. Remove supernatant. Repeat by adding another 50 microliters of dimethylsulfoxide, precipitating with tert-butyl methyl ether, and centrifuging. After ether has completely evaporated from tube, add 250 microliters of dimethylsulfoxide and store in −20 degrees C. freezer.

2. Addition of the Other Components

A solution of 70 nmol of fusogenic peptide is placed in a 12×75 culture tube and the solvents evaporated. Then, 10 µl of dimethylformamide (or dimethylsulfoxide) are added to dissolve the peptide, followed by 0.2 ml of 250 mM cholate in PB buffer.

A solution of 700 nmol of 14:1-PC is placed in a 12×75 culture tube, mixed with approximately 0.25 ml of 95% distilled ethanol, and the solvents evaporated. The two solutions above (the lipid-peptide conjugate and the fusogenic peptide) are transferred to the tube with this 14:1-PC. If necessary, the volume is adjusted to 0.7 ml with 250 mM cholate in PB buffer. 12 µg DNA (in 10–20 µl Tris-EDTA (TE) buffer) is added to the solution containing the other components.

The final mixture is placed in dialysis tubing, and dialyzed 3 times against a minimum of 1 L of PB buffer with at least 6 hours between changes of dialysis buffer. After dialysis, the sample is diluted to 1 ml in PB buffer, and refrigerated before use.

In one embodiment, the range of 14:1-PC is from about 300 nmol to about 1500 nmol. In this embodiment, lipid/ protein ratios range from about 5:1 mol/mol to about 100:1 mol/mol. The optimum amount of lipid and the optimum lipid/protein ratio, may vary depending upon cell type in cell culture, the organ system in vivo, the quantities of the two components added for assembly with DNA, and the material to be encapsulated. Thus, the exact amounts of each component may vary.

Example B

Another liposome complex is formed as follows.

Components of the System

DNA plasmid containing beta-galactosidase gene –7.9 kilobase pairs, (Life Technologies #10586-014). 50 micrograms are contained in 10 millimolar Tris buffer with 1 millimolar EDTA at approximately 1 milligram per milliliter.

The fusogenic peptide is SEQ ID NO:3. 20 nmol are contained in a solvent of acetonitrile/water/trifluoroacetic acid 50:50:0.1 (v/v/v) at approximately 500 nmol per milliliter.

The nuclear localization signal peptide is SEQ ID NO: 5 coupled to dioleoylphosphatidylethanolamine using the cross-linking reagent MBS 3-maleimidobenzoic acid N-hydroxysuccinimide ester). 200 nmol are contained in a solvent of dimethylsulfoxide at approximately 4 micromoles per milliliter.

The lipid component is dimyristoleoylphosphatidylcholine. 350 nmol are contained in a solvent of chloroform at approximately 20 micromoles per milliliter.

Procedure

Into a 12×75 culture tube, place both a) the fusogenic peptide and b) the lipid-NLSP conjugate. Evaporate to dryness with nitrogen gas with mild heating.

Add the lipid component. Add a few drops of distilled 95% ethanol. Evaporate to dryness with nitrogen gas with mild heating.

Add 10 microliters of dimethylformamide to the tube. All components will dissolve into solution.

Add 1.0 milliliters of a solution of 250 millimolar cholate (the anion of cholic acid) in 10 millimolar phosphate buffer, pH 8.0.

Add 50 micrograms of DNA plasmid.

Transfer solution to a 15 ml sterile plastic tube, and add 9.0 milliliters of sterile PB buffer (10 millimolar, pH 8.0).

Place solution in a dialysis bag, and dialyze three times against 1 liter of sterile PB buffer, with 6 hours or more between changes of dialysis buffer.

After dialysis, place sample into ultracentrifuge tube(s), and centrifuge at approximately 100,000×g for 1 hour.

Remove supernatant, and resuspend pellet in approximately 100 microliters of sterile PB buffer. The resuspended pellet is the liposome preparation.

The liposome complexes are administered to cells to deliver at least up to 10 micrograms of DNA per 35 mm culture dish of cells. If higher transfection efficiency is desired, replace the medium with fresh medium plus additional liposome preparation (10 micrograms DNA plasmid) every four hours up to 16 hours from the start of the procedure.

This procedure shows approximately 10–20% cells exhibiting reporter gene expression given one addition of liposomes at the start of the procedure. If liposomes are added repeatedly at 0 hour, 4 hour, 8 hour, and 12 hour from the start of the experiment, greater than 50% of the cells show reporter gene expression.

SPECIFIC EXAMPLE 2

Assessment of Fusion Activity

Fusion activity is evaluated by assaying for reporter gene expression after incubating fusogenic liposomes with mammalian cells in culture.

In a typical procedure using 3T3 cells, approximately 50,000 3T3 cells are added to each of several 35-mm tissue culture wells, and grown in Minimal Essential Medium+ 10% fetal calf serum for 48 hours. The medium is replaced with fresh medium (plus 10% serum). Liposome complexes are added and incubated with the cells for 24 hours. The liposome complexes were prepared with a composition of 112 nmol of N-iodoacetyl DOPE reacted with 135 nmol of nuclear localization signal peptide (SEQ ID NO: 4); 1400 nmol 14:1 PC; 93 nmol fusogenic peptide (SEQ ID NO:3); and 12 micrograms DNA plasmid with either luciferase reporter gene or beta-galactosidase reporter gene. The medium is replaced with fresh medium+serum and the cells incubated an additional 12 hours. (The range of liposome concentrations is: 0.1 to 5 µg DNA. The range of times of liposome-cell incubations is: 1–24 hours. The range of time between addition of liposomes and assay of reporter gene expression: 24–48 hours.)

Luciferase reporter gene expression is assayed using the assay kits and procedures of the Promega luciferase assay system. Beta-galactosidase activity is measured by rinsing the cells with phosphate-buffered saline, fixing the cells for 15 minutes with a solution of 2% formaldehyde+0.2% glutaraldehyde in phosphate-buffered saline (PBS), rinsing with PBS, and incubating the cells overnight in a solution of X-Gal reagent (5-bromo-4-chloro-3-indolyl β-D-galactopyranoside) in PBS+20 mM ferricyanide+20 mM ferrorcyanide+2 mM magnesium chloride.

SPECIFIC EXAMPLE 3

Nature of the Components

Liposome complexes were prepared as described in Example 2 except that one of the components from the formulation was systematically omitted, as indicated in FIG. 1. In sample 6 at the far right of FIG. 1, the lipid was omitted but then replaced by an equal quantity of 1,2-dioleoylphosphatidylcholine.

HeLa cells were added to 6-well Falcon tissue culture plates (50K cells per well, each well approximately 35 mm diameter) and cultured for 48 hours in the following culture medium: Minimal Essential Medium, plus 1% non-essential amino acids, plus 10% fetal calf serum. At the beginning of the experiment the medium was replaced with the same medium (with 10% serum) plus antibiotics+antimycotic.

Each 35 mm well of HeLa cells was incubated for 12 hours with liposomes containing 1 µg DNA. The wells were rinsed with fresh medium+serum and incubated for an additional 24 hours. Cells were rinsed twice at room temperature with phosphate-buffered saline, then lysed with 0.25 ml lysis buffer provided in the luciferase enzyme assay kit purchased from Promega (Madison, Wis.). After 30 minutes, luciferase activity was assayed by mixing 50 µl of cell lysate with 50 µl of Promega luciferase assay buffer. Activity was measured using a scintillation counter with coincidence counting in effect, hence is reported as the square root of the counts per minute. Error bars are standard error of the mean, n=4.

The results are shown in FIG. 1. The formulation having non-cationic lipid, a fusogenic peptide, nucleic acid to be delivered intranuclearly, and a positively charged peptide anchored to a lipid for use in assembly worked significantly better than any other combination.

SPECIFIC EXAMPLE 4

Concentration Ranges for Liposome-Cell Incubation—HeLa Cells

Example 4 indicates the effect of the concentration of liposome complex prepared as described in Example 2, and the effect of serum (10% in the cell culture medium) on reporter gene expression in HeLa cells.

Liposome complexes were prepared as described in Example 2 with luciferase reporter gene. Cell culture was performed as described in Example 3 with the following changes. Prior to the addition of the liposome complexes, all cells were rinsed 3 times with medium without serum. To half the wells was added medium without serum (with antibiotics and antimycotic) and to the other wells was added medium with serum. Liposome complexes were added at the indicated concentration for a total of 5 hours. After that time, the medium was removed and all cells received medium+10% serum for an additional 31 hours prior to assay for luciferase reporter gene activity. Error bars are standard error of the mean, n=4.

The results are shown in FIG. 2 which shows higher levels of activity are achieved in the presence of serum (10% of total culture medium) compared to the absence of serum.

SPECIFIC EXAMPLE 5

Concentration Ranges for Liposome-Cell Incubation—3T3 Cells

Example 5 indicates the effects of concentration of liposome complex prepared as described in Example 2 and the effect of serum on reporter gene expression, this time with NIH 3T3 cells. Cell culture was performed as described in Example 3 with the following changes: Prior to the addition of liposomes, all cells were rinsed 3 times with medium without serum. To half the wells was added medium without serum (with antibiotics and antimycotic) and to the other wells was added medium with serum. Liposomes were added at the indicated concentration. After 6 hours, liposomes were removed and all wells then incubated with medium+10% serum for a total transfection time of 36 hours. Values are mean±SEM, n=4

The results are shown in FIG. 3. Higher levels of activity are achieved in the presence of serum (10% of total culture medium) compared to the absence of serum.

SPECIFIC EXAMPLE 6

Percentage of Cells Transfected

Example 6 indicates levels of transfection observed using HeLa cells and the liposome complex. Liposome complexes were prepared as described in Example 2 with the β-galactosidase reporter gene. HeLa cells were incubated with liposomes containing 1.25 µg DNA in two successive 6 hour incubations, always in medium+10% serum. The liposome complexes were removed and cells incubated an additional 12 hours in medium+10% serum. The cells were rinsed with phosphate-buffered saline, then fixed for 30 minutes at room temperature with PBS containing 0.2% glutaraldehyde and 2.0% formaldehyde. The cells were rinsed 3 times with PBS, then incubated overnight with 1.0 mg X-Gal reagent in 1.5 ml of a solution of phosphate-buffer saline plus 20 mM potassium ferrocyanide, 20 mM potassium ferricyanide, and 2 mM magnesium chloride.

FIG. 4 shows the results. Transfected cells are estimated to be between 20–30% of total cells.

SPECIFIC EXAMPLE 7

Time Course of Luciferase Gene Expression

HeLa cells were seeded into six-well tissue culture plates at 50K cells per well. After 48 hours and just prior to the experiment, the medium was changed to 1.5 ml per well of MEM medium+1% non-essential amino acids+10% fetal calf serum+antibiotics.

The liposome complexes prepared as described in Example 2 with the luciferase reporter gene were added to the wells at a concentration of 1 µg DNA per well.

After 12 hours, medium was removed and replaced with fresh medium+non-essential amino acids+10% fetal calf serum+antibiotics.

At each of the indicated times, 4 wells were rinsed twice with phosphate-buffered saline, then the cells lysed with 250 µl of Promega luciferase assay kit lysis buffer. After 15 minutes, an aliquot of the lysate was diluted 1:5 in lysis buffer. For assay, a 20 µl aliquot of the diluted sample was mixed with 100 µl of Promega luciferase assay buffer. Activity was determined using a scintillation counter, with coincident counter on. Values are mean±s.e.m, n=4.

The results are shown in FIG. 5.

SPECIFIC EXAMPLE 8

Delivery of Fluorescently-Labeled Dextran to the Cell Cytoplasm

HeLa cells were plated on circular glass cover slips and grown in medium+10% fetal calf serum. Liposome complexes were prepared as follows: Eight micromoles of 14:1 PC, two micromoles of dinervonoylphosphatidylcholine (24:1 PC) and 0.4 micromoles of fusogenic peptide (SEQ ID NO: 1) were placed in a 13×100 culture tube and the solvents evaporated. A solution of 0.5 milliliters of phosphate-buffered saline (PBS) containing 25 mg/ml of neutral, 10,000 MW rhodamine-B-labeled dextran (Molecular Probes, Eugene, OR) was added, and liposomes formed by sonication with a probe sonicator. Unencapsulated dye was removed by chromatography through 15 ml of G-100 Sephadex in PBS buffer. The two components (positively charged peptide and cross-linking phosphatidylethanolamines) used for the self-assembly with DNA were omitted in this experiment. Cells were incubated overnight with liposomes (approximately 0.5 micromoles of lipid for each 35 mm dish of cells) containing the encapsulated dye. Cells were rinsed 3 times in PBS buffer containing 1 mM $Ca^{2+}$.

The results are shown in FIG. 6. Cytoplasmic fluorescence was observed, as indicated by the nuclear shadow seen in several cells with the nucleus in the plane of focus (arrows).

SPECIFIC EXAMPLE 9

Addition of a Polymer Coating Prolongs Liposome Complexes in Serum

A conjugate of DOPE and polyethylene glycol polymer (average molecular weight 5000) containing a disulfide linkage was prepared according to methods described in Kirpotin, et al., FEBS Letters, 388(2–3):115–8 (1996). The conjugate was stored at −20 degrees in ethanol at a concentration of approximately 2 micromoles per milliliter. Liposomes were then prepared as described in specific example 2 with the exception that a 3-fold greater volume of 250 mM cholate in PB buffer was used in each step. The liposomes were prepared with the following compositions: 135 nmol of nuclear localization signal peptide (SEQ ID NO: 6) with each molecule of nuclear localization signal peptide coupled to two molecules of N-iodoacetyl DOPE via the two cysteine amino acids; 2100 nmol of 14:1 PC; and 210 nmol fusogenic peptide (SEQ ID NO:3). To one preparation was added 70 nmol of DOPE-polyethylene glycol conjugate, at the same point where the. 14:1 PC was added to the preparation. A separate preparation was made without polymer.

In this Example 9, a polymer coating has been added to the formulation (lipid, fusogenic peptide, DNA, and a nuclear localization signal anchored to a lipid) in such a way that expression of the fusogenic activity of the liposome complex is not impaired. The addition of the polymer coating 1) makes the liposomes resistant to serum inactivation (FIG. 7), 2) extends transfection times following a single addition of liposomes (FIGS. 8A and 8B), and 3) reduces particle size (FIGS. 9A and 9B) in comparison to liposome complexes without the polymer coating. 125K HepG2 cells were grown in Falcon six-well plates for 48 hours. Liposome complexes with and without polymer coating were either added directly to the cells, or first preincubated in fetal calf serum for 5 hours at 37° C. [Liposomes in PBS/fetal calf serum, 1/1 (v/v)]. Liposome-cell incubations (1 µg DNA plasmid) were carried out for 48 hours, and assayed for luciferase activity as described in Example 3. The results are shown in FIG. 7.

SPECIFIC EXAMPLE 10

Polymer-Coated, Fusogenic Liposomes Exhibit Extended Transfection Times in Cell Culture 50K Hela cells were grown in Falcon six-well plates for 48 hours. Liposome complexes as described in Example 2 with and without polymer coating, in medium+10% fetal calf serum, were added at a concentration of 1 µg DNA plasmid per well. (DNA plasmid: Promega pGL3 control vector, 5.3 kb). Cells were lysed at the indicated times, and 20 µl aliquots (250 µl total volume per well) were assayed for luciferase activity using a scintillation counter and the Promega luciferase assay kit.

FIG. 8A shows the time course of transfection resulting from liposome complexes without polymer coating and FIG. 8B shows the time course of transfection resulting from liposome complexes with polymer coating.

SPECIFIC EXAMPLE 11

Addition of Polymer Coating Reduces Liposome Particle Size

The liposome complexes, with luciferase pGL3 plasmid (5.3 kb), were prepared with (FIG. 9B) and without (FIG. 9A) the polymer coating. Liposome particle size distributions were measured by dynamic light scattering on a Microtrac Ultrafine Particle Analyzer (approximately 3 µg DNA plasmid per analysis).

FIG. 9A shows that liposomes without the polymer coating exhibited a particle size distribution from approximately 60 nm to 2000 nm. Liposomes prepared with the polymer coating (FIG. 9B) exhibited a size distribution ranging from approximately 40 nm to 450 nm.

CONCLUDING REMARKS

The foregoing description details specific methods which can be employed to practice the present invention. Having detailed such specific methods, those skilled in the art will well enough know how to devise alternative reliable methods at arriving at the same information by using the fruits of the present invention. Thus, however detailed the foregoing may appear in text, it should not be construed as limiting the overall scope thereof; rather, the ambit of the present invention is to be determined only by the lawful construction of the appended claims. All documents cited herein are hereby expressly incorporated by reference.

SEQUENCE LISTING

<160> NUMBER OF SEQ ID NOS: 15

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: synthetic

<400> SEQUENCE: 1

Phe Pro Ile Pro Leu Pro Tyr Cys Trp Leu C ys Arg Ala Leu Ile Lys
 1               5                  10                  15

Arg Ile Gln Ala Met Ile Pro Lys Gly
            20                  25

<210> SEQ ID NO 2
<211> LENGTH: 31
<212> TYPE: PRT
<213> ORGANISM: Artificial Sequence
<220> FEATURE:
<223> OTHER INFORMATION: Description of Artificial Sequence: synthetic

<400> SEQUENCE: 2

Phe Pro Ile Pro Leu Pro Ile Pro Leu Pro I le Pro Tyr Cys Trp Leu
 1               5                  10                  15

```
Ala His Ala Leu Ile His His Ile Gln Ala Met Ile Pro His Gly
            20                  25                  30

<210> SEQ ID NO 3
<211> LENGTH: 31
<212> TYPE: PRT
<213> ORGANISM: Artificial Sequence
<220> FEATURE:
<221> NAME/KEY: SITE
<222> LOCATION: (16)
<223> OTHER INFORMATION: The amino acid at position 16 represents
      Norleu.
<221> NAME/KEY: SITE
<222> LOCATION: (20)..(21)
<223> OTHER INFORMATION: The amino acid at positions 20, 21 represents
      Norleu.
<221> NAME/KEY: SITE
<222> LOCATION: (24)
<223> OTHER INFORMATION: The amino acid at position 24 represents
      Norleu.
<221> NAME/KEY: SITE
<222> LOCATION: (28)
<223> OTHER INFORMATION: The amino acid at position 28 represents
      Norleu.
<223> OTHER INFORMATION: Description of Artificial Sequence: synthetic

<400> SEQUENCE: 3

Phe Pro Ile Pro Leu Pro Ile Pro Leu Pro Ile Pro Tyr Cys Trp Xaa
 1               5                  10                  15

Ala His Ala Xaa Xaa His His Xaa Gln Ala Met Xaa Pro His Gly
            20                  25                  30

<210> SEQ ID NO 4
<211> LENGTH: 13
<212> TYPE: PRT
<213> ORGANISM: Polyomavirus large T antigen
<220> FEATURE:
<223> OTHER INFORMATION: Description of Artificial Sequence: synthetic

<400> SEQUENCE: 4

Cys Gly Tyr Gly Val Ser Arg Lys Arg Pro Arg Pro Gly
 1               5                  10

<210> SEQ ID NO 5
<211> LENGTH: 10
<212> TYPE: PRT
<213> ORGANISM: HIV-1 matrix protein

<400> SEQUENCE: 5

Cys Gly Lys Lys Lys Tyr Lys Leu Lys His
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 6

Cys Gly Cys Gly Lys Lys Lys Tyr Lys Leu Lys His
 1               5                  10

<210> SEQ ID NO 7
<211> LENGTH: 15
<212> TYPE: PRT
<213> ORGANISM: Artificial Sequence
<220> FEATURE:
<221> NAME/KEY: SITE
```

```
<222> LOCATION: (1)
<223> OTHER INFORMATION: The Xaa at position 1, 5, 6, 9, and 13 is any
      naturally occuring or synthetic hydrophobic amino
      acid.
<223> OTHER INFORMATION: Description of Artificial  Sequence: synthetic
<221> NAME/KEY: SITE
<222> LOCATION: (2)
<223> OTHER INFORMATION: The Xaa at position 2, 4, 10, 12, and 14 can be
      any amino acid.

<400> SEQUENCE: 7

Xaa Xaa His Xaa Xaa Xaa His His Xaa Xaa His Xaa Xaa Xaa His
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial  Sequence: synthetic

<400> SEQUENCE: 8

Leu Ala His Ala Leu Leu His His Leu Ala His Ala Leu Ala His
 1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial  Sequence: synthetic

<400> SEQUENCE: 9

Ile Ala His Ala Ile Ile His His Ile Ala His Ala Ile Ala His
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial  Sequence: synthetic

<400> SEQUENCE: 10

Leu Ala His Ala Ile Leu His His Ile Ala His Ala Leu Ala His
 1               5                  10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial  Sequence: synthetic

<400> SEQUENCE: 11

Phe Ala His Ala Phe Phe His His Phe Ala His Ala Phe Ala His
 1               5                  10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial  Sequence: synthetic

<400> SEQUENCE: 12

Leu Leu His Leu Leu Leu His His Leu Leu His Leu Leu Leu His
 1               5                  10                  15
```

```
<210> SEQ ID NO 13
<211> LENGTH: 15
<212> TYPE: PRT
<213> ORGANISM: Artificial Sequence
<220> FEATURE:
<223> OTHER INFORMATION: Description of Artificial  Sequence:  synthetic

<400> SEQUENCE: 13

Leu Ala His Ala Leu Leu Ser His Leu Ala H is Ala Leu Ala Ser
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial  Sequence:  synthetic

<400> SEQUENCE: 14

Leu Ala His Ala Leu Leu Glu His Leu Ala G lu Ala Leu Ala His
 1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial  Sequence:  synthetic

<400> SEQUENCE: 15

Leu Ser His Ser Leu Leu His His Leu Ser H is Ser Leu Ser His
 1               5                  10                  15
```

What is claimed is:

1. A liposome complex comprising:
   a fusogenic peptide, wherein the fusogenic peptide is selected from the group consisting of a peptide comprising the amino acid sequence of SEQ ID NO: 7 and variants of an N-terminal pulmonary surfactant B (SP-B) peptide, wherein said N-terminal SP-B peptide consists essentially of the first 25 amino acids of the N-terminus of an SP-B protein, wherein each of said variants comprises one or more changes to the native sequence of said N-terminus selected from the group consisting of:
   1) substitution of one or more lysine and/or one or more arginine of the hydrophilic stripe of the amphipathic alpha helix with histidine;
   2) substitution of one or more leucine and/or one or more isoleucine from the hydrophobic stripe of the amphipathic alpha helix with norleucine;
   3) lengthening the membrane anchoring sequence in the first 6 positions of the N-terminal by inserting additional membrane anchoring amino acids; and
   4) replacing the C-terminus carboxylic acid group with an amide group;
   a non-cationic lipid; and
   a substance to be delivered into a cell.

2. The complex of claim 1 wherein the non-cationic lipid is a zwitterionic, neutral, or anionic phospholipid comprising saturated and/or unsaturated fatty acid chains having a length of 8 to 14 carbons.

3. The complex of claim 1 wherein the substance to be delivered is a nucleic acid.

4. The complex of claim 1 further comprising a positively charged companion peptide coupled to a cross-linking lipid.

5. The complex of claim 4 wherein the positively charged companion peptide is a nuclear localization signal peptide.

6. The complex of claim 1 further comprising a ligand for cell targeting.

7. The complex of claim 1, wherein said liposome complex is capable of delivering said substance to the cytoplasm and/or the inside of the nucleus of a cell.

8. A method for delivering a substance to a cell comprising administering to a host a liposome complex comprising a fusogenic peptide; a non-cationic lipid; and a substance to be delivered into a cell, wherein the fusogenic peptide is selected from the group consisting of a peptide comprising the amino acid sequence of SEQ ID NO: 7 and variants of an N-terminal pulmonary surfactant B (SP-B) peptide, wherein said N-terminal SP-B peptide consists essentially of the first 25 amino acids of the N-terminus of an SP-B protein, wherein each of said variants comprises one or more changes to the native sequence of said N-terminus selected from the group consisting of:
   1) substitution of one or more lysine and/or one or more arginine of the hydrophilic stripe of the amphipathic alpha helix with histidine;
   2) substitution of one or more leucine and/or one or more isoleucine from the hydrophobic stripe of the amphipathic alpha helix with norleucine;
   3) lengthening the membrane anchoring sequence in the first 6 positions of the N-terminal; and
   4) replacing the C-terminus carboxylic acid group with an amide group.

9. The method of claim 8 wherein the host is a human cell.

10. The method of claim 8 wherein the non-cationic lipid is a zwitterionic, neutral, or anionic phospholipid comprising saturated and/or unsaturated fatty acid chains having a length of 8 to 14 carbons.

11. The method of claim 8 wherein the substance to be delivered is a nucleic acid.

12. The method of claim 8 wherein the complex further comprises a positively charged companion peptide coupled to a cross-linking lipid.

13. The method of claim 12 wherein the positively charged companion peptide is a nuclear localization signal peptide.

14. The method of claim 8 wherein the complex further comprises a ligand for cell targeting.

15. The method of claim 8 wherein the cell is a tumor cell.

16. A fusogenic peptide selected from the group consisting of a peptide comprising the amino acid sequence of SEQ ID NO: 7 and variants of an N-terminal pulmonary surfactant B (SP-B) peptide, wherein said N-terminal SP-B peptide consists essentially of the first 25 amino acids of the N-terminus of an SP-B protein, wherein each of said variants comprises one or more changes to the native sequence of said N-terminus selected from the group consisting of:
   1) substitution of one or more one or more lysine and/or one or more arginine of the hydrophilic stripe of the amphipathic alpha helix with histidine;
   2) substitution of one or more leucine and/or one or more isoleucine from the hydrophobic stripe of the amphipathic alpha helix with norleucine;
   3) lengthening the membrane anchoring sequence in the first 6 positions of the N-terminal; and
   4) replacing the C-terminus carboxylic acid group with an amide group, complexed with a non-cationic lipid which is a zwitterionic, neutral, or anionic phospholipid comprising saturated and/or unsaturated fatty acid chains having a length of 8 to 14 carbons.

17. A method for assembling a liposome complex for delivering a substance into a cell comprising:
   combining a fusogenic peptide, a non-cationic lipid and a substance to be delivered to the cytoplasm of the cell in amounts effective to form a liposome complex, wherein the fusogenic peptide is selected from the group consisting of a peptide consisting essentially of the amino acid sequence of SEQ ID NO:1, a peptide comprising the amino acid sequence of SEQ ID NO: 7, and variants of an N-terminal pulmonary surfactant B (SP-B) peptide, wherein said N-terminal SP-B peptide consists essentially of the first 25 amino acids of the N-terminus of an SP-B protein, wherein each of said variants comprises one or more changes to the native sequence selected from the group consisting of:
      1) substitution of one or more one or more lysine and/or one or more arginine of the hydrophilic stripe of the amphipathic alpha helix with histidine;
      2) substitution of one or more leucine and/or one or more isoleucine from the hydrophobic stripe of the amphipathic alpha helix with norleucine;
      3) lengthening the membrane anchoring sequence in the first 6 positions of the N-terminal; and
      4) replacing the C-terminus carboxylic acid group with an amide group.

18. The method of claim 17 further comprising combining a positively charged companion peptide so as to conjugate the companion peptide to the liposome complex.

19. The method of claim 18 wherein the positively charged companion peptide is a nuclear localization signal peptide.

20. A kit comprising a fusogenic peptide and a non-cationic lipid, wherein the fusogenic peptide is selected from the group consisting of a peptide comprising the amino acid sequence of SEQ ID NO: 7 and variants of an N-terminal pulmonary surfactant B (SP-B) peptide, wherein said N-terminal SP-B peptide consists essentially of the first 25 amino acids of the N-terminus of human SP-B protein, wherein each of said variants comprises one or more changes to the native sequence of said N-terminus selected from the group consisting of:
   1) substitution of one or more one or more lysine and/or one or more arginine of the hydrophilic stripe of the amphipathic alpha helix with histidine;
   2) substitution of one or more leucine and/or one or more isoleucine from the hydrophobic stripe of the amphipathic alpha helix with norleucine;
   3) lengthening the membrane anchoring sequence in the first 6 positions of the N-terminal; and
   4) replacing the C-terminus carboxylic acid group with an amide group.

21. The kit of claim 20 wherein the peptide and lipid are complexed.

22. A liposome complex comprising:
   (a) a fusogenic peptide comprising the amino acid sequence of SEQ ID NO: 7:
   (b) a non-cationic lipid; and
   (c) a substance to be delivered to the cytoplasm and/or the inside of the nucleus of a cell.

23. The complex of claim 22 wherein the non-cationic lipid is a zwitterionic, neutral, or anionic phospholipid comprising saturated and/or unsaturated fatty acid chains having a length of 8 to 14 carbons.

24. The complex of claim 22 wherein the substance to be delivered is a nucleic acid.

25. The complex of claim 22 further comprising a positively charged companion peptide coupled to a cross-linking lipid.

26. The complex of claim 25 wherein the positively charged companion peptide is a nuclear localization signal peptide.

27. The complex of claim 22 further comprising a ligand for cell targeting.

28. A method for delivering a substance to a cell comprising:
   administering to a host a liposome complex comprising:
      a fusogenic peptide comprising the amino acid sequence of SEQ ID NO: 7;
      a non-cationic lipid; and
      a substance to be delivered to the cytoplasm and/or the inside of the nucleus of the cell.

29. The method of claim 28 wherein the host is a human cell.

30. The method of claim 28 wherein the non-cationic lipid is a zwitterionic, neutral, or anionic phospholipid comprising saturated and/or unsaturated fatty acid chains having a length of 8 to 14 carbons.

31. The method of claim 28 wherein the substance to be delivered is a nucleic acid.

32. The method of claim 28 wherein the complex further comprises a positively charged companion peptide coupled to a cross-linking lipid.

33. The method of claim 32 wherein the positively charged companion peptide is a nuclear localization signal peptide.

34. The method of claim 28 wherein the complex further comprises a ligand for cell targeting.

35. A fusogenic peptide comprising the amino acid sequence of SEQ ID NO: 7, complexed with a non-cationic lipid which is a zwitterionic, neutral, or anionic phospholipid comprising saturated and/or unsaturated fatty acid chains having a length of 8 to 14 carbons.

36. A method for assembling a liposome complex for delivering a substance to the cytoplasm and/or the inside of a nucleus of a cell comprising:

combining:
- a fusogenic peptide comprising the amino acid sequence of SEQ ID NO: 7;
- a non-cationic lipid; and
- a substance to be delivered to the cytoplasm of the cell in amounts effective to form a liposome complex.

37. The method of claim 36 further comprising combining a positively charged companion peptide so as to conjugate the companion peptide to the liposome complex.

38. The method of claim 37 wherein the positively charged companion peptide is a nuclear localization signal peptide.

39. A kit comprising a fusogenic peptide comprising the amino acid sequence of SEQ ID NO: 7 and a non-cationic lipid.

40. The kit of claim 39 wherein the peptide and lipid are complexed.

* * * * *